United States Patent [19]
Amrein et al.

[11] Patent Number: 5,735,852
[45] Date of Patent: Apr. 7, 1998

[54] CLAMP JAW FOR A SPINAL AFFIXATION DEVICE

[75] Inventors: Thomas Amrein, Horw; Konrad Tagwerker, Basel; Bernhard Jeanneret, Mörschwil, all of Switzerland

[73] Assignee: Synthes (U.S.A.), Paoli, Pa.

[21] Appl. No.: 776,236

[22] PCT Filed: May 22, 1995

[86] PCT No.: PCT/CH95/00114

§ 371 Date: Jan. 10, 1997

§ 102(e) Date: Jan. 10, 1997

[87] PCT Pub. No.: WO96/37159

PCT Pub. Date: Nov. 28, 1996

[51] Int. Cl.[6] ............................................. A61F 5/00
[52] U.S. Cl. ........................... 606/61; 606/72; 606/73
[58] Field of Search .............................. 606/61, 73, 72

[56] References Cited

U.S. PATENT DOCUMENTS 5,133,717  7/1992  Chopin ................................ 606/61
5,147,360  9/1992  Dubousset ......................... 606/61
5,403,314  4/1995  Currier ............................... 606/61

FOREIGN PATENT DOCUMENTS 0441668  8/1991  European Pat. Off. .
0468264  1/1992  European Pat. Off. .
0553424  8/1993  European Pat. Off. .
9314721  8/1993  WIPO .
9414385  7/1994  WIPO ................................. 606/61

Primary Examiner—Michael Buiz
Assistant Examiner—Julian W. Woo
Attorney, Agent, or Firm—Pennie & Edmonds

[57] ABSTRACT

The invention concerns a clamp for a spinal affixation device which has a base body (1) crossed by a duct (2) having a longitudinal axis (3) for receiving a longitudinal support. The clamp includes a substantially planar extension (4) continuing the base body (1) and crossed by a screw hole (5) having a center axis (6) for receiving a bone screw. The duct (2) can longitudinally and rotationally lock in place a longitudinal support which is inserted therein. The longitudinal axis (3) of the duct (2) and the center axis (6) of the screw hole (5) form skewed straight lines of constant spacing (7) at a distance in the range of 4 to 10 mm.

12 Claims, 4 Drawing Sheets

CLAMP JAW FOR A SPINAL AFFIXATION DEVICE

TECHNICAL FIELD

The invention relates to a clamp for a spinal affixation device.

BACKGROUND ART

Such a clamp is known for instance from European patent Application No. A 0,553,424. It is used to affix the individual intravertebral body in a mutually defined position, a number of bone screws implanted into the intravertebral bodies being fastened by such clamps onto a longitudinal support running in the direction of the spine.

The known clamp disclosed in .the European patent Application No. A 0,553,424 is in three parts in order to allow adjusting both the distance and the angular position between the bone screw and the longitudinal support. It is precisely this high adaptability which substantially hampers surgery. The angle and distance between the bone screw and the longitudinal support must be adjusted in-situ. This constraint entails simultaneously setting the clamp and the longitudinal support on one hand and on the other hand fastening the affixation screw to achieve the desired configuration. Thereby a spanner wrench must be used to apply a torque opposing the tightening torque of the affixation screw to prevent the assembly as a whole from rotating while this affixation screw is being tightened. Mounting several such assemblies within the confines of the cervical spine is exceedingly laborious because the parts to be assembled are not easily seen and because the surgeons hamper one another when lining up and affixing the individual components.

SUMMARY OF THE INVENTION

The object of the invention is palliation. It addresses the task of creating an easily and economically manufactured clamp making superfluous intra-surgery adjustment of the mutual distances and angles of the structures held by the clamp and thereby reducing surgery time while increasing reliability.

The object of the invention is solved by a clamp having a base body (1) crossed by a duct (2) with longitudinal axis (3) receiving a longitudinal support (15), the duct (2) being fitted with means allowing to rotationally and longitudinally lock in place the inserted longitudinal support, an extension (4) continuing the base body (1) and crossed by a screw hole (5) evincing a center axis (6) and receiving a bone screw (16). The longitudinal axis (3) and the center axis (6) define skewed straight lines. The extension (4) is mounted at an angle of 0° to 45° with regard to the plane of projection (11), and the plane of projection (11) is formed by the longitudinal axis (3) and the orthogonal line (10) which is perpendicular to the longitudinal axis (3) as well as to the longitudinal axis (9). In this device, the spacing (7) between the longitudinal axis (3) and the center axis (6) is constant and within the range of 4–10 mm; and the extension (4) is substantially tabular.

Preferably, the spacing (7) is within the range of 5–8 mm, and more preferably is from 5.8 to 6.7 mm. Also, the length of the duct (2) measured in the axial direction is from 5 to 7 mm, and more preferably from 5.7 to 6.3 mm. Furthermore, the duct (2) evinces a diameter in the range of 3.0 to 4.5 mm, and preferably from 3.2 to 3.8 mm.

Advantageously, the means locking a longitudinal support inserted into the duct (2) include, inside the base body (1), a threaded borehole (8) having a longitudinal axis (9) orthogonal to the plane (11), and an adjusting screw (17) being insertable into said borehole (8). The screw hole (5) is concave, preferably spherical, in the seating zone for the head of a bone screw inserted into the hole (5).

In a most preferred arrangement, the clamp is integral.

The clamp may have an azimuth angle (12), subtended by the longitudinal axis (6) and the longitudinal axis (3) in the plane of projection (11) formed by the longitudinal axis (3) and the orthogonal line (10), which is within the range of +20° to 30°. The clamp may also have an azimuth angle (12) which is within the range of −5° to +5° C., and a cranial angle (13), subtended by the center axis (6) and the longitudinal axis (3) in the plane of projetion (11) formed by the longitudinal axis (3) and the longitudinal axis (9), is within the range of either 42.5° to 50° or 80° to 100°.

The extension (4) is substantially tabular and is mounted preferably at an angle of 0° to 45° to the plane of projection (11). In this arrangement, the upper and lower surfaces of the tabular extension (4) are essentially parallel to each other. Also, the duct (2) may be open on the side opposite the extention (4) in order to receive a longitudinal support (15).

Essentially the advantages of the invention may be construed as the clamp of the invention predetermining by its geometry the anatomically proper position of the bone screw relative to the longitudinal support. Accordingly the clamp of the invention no longer requires being adjusted in-situ as is the case in the state of the art, and as a result time is saved and the reliability of anatomically proper anchoring to the bone is increased. Once in-situ, no more is needed than the bone screws being screwed through the clamps into the bone.

The invention offers a further advantage over the state of the art by the absence of danger that connections inside the clamp may come loose, since this clamp is integral.

BRIEF DESCRIPTION OF THE DRAWINGS

The invention and further embodiments of it are elucidated below in relation to the partly schematic drawings of an illustrative embodiment.

DETAILED DESCRIPTION OF THE PREFERRED EMBODIMENTS

Figure 1:
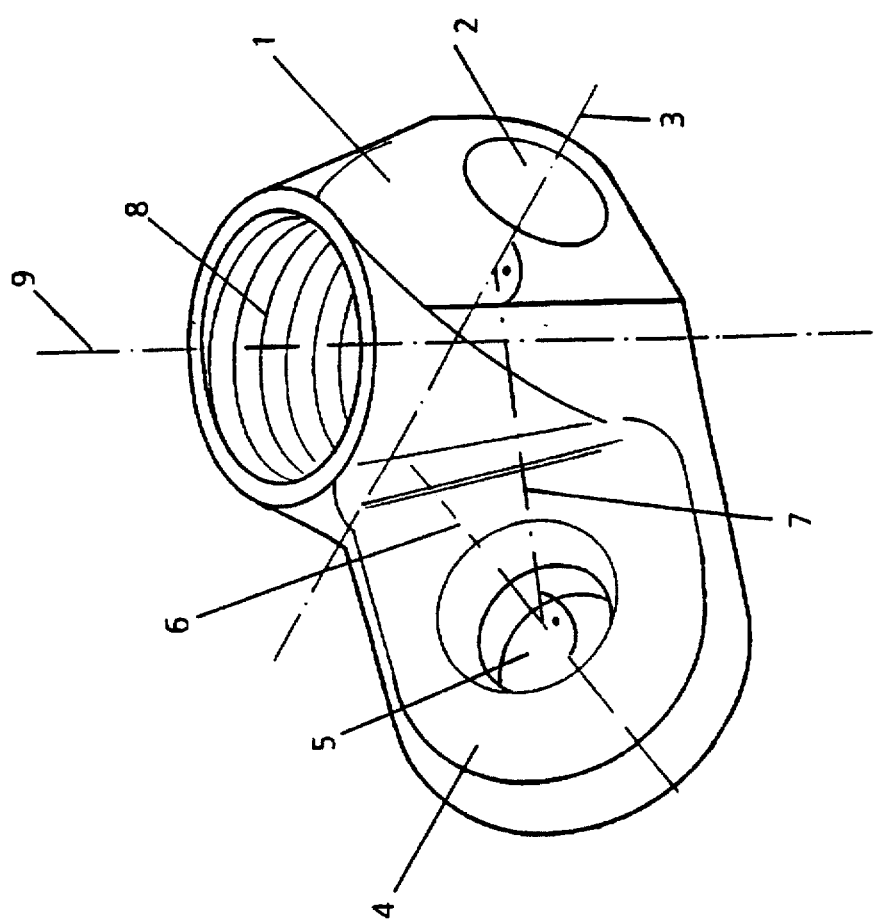
FIG. 1 is a perspective of the clamp of the invention.
Figure 4:
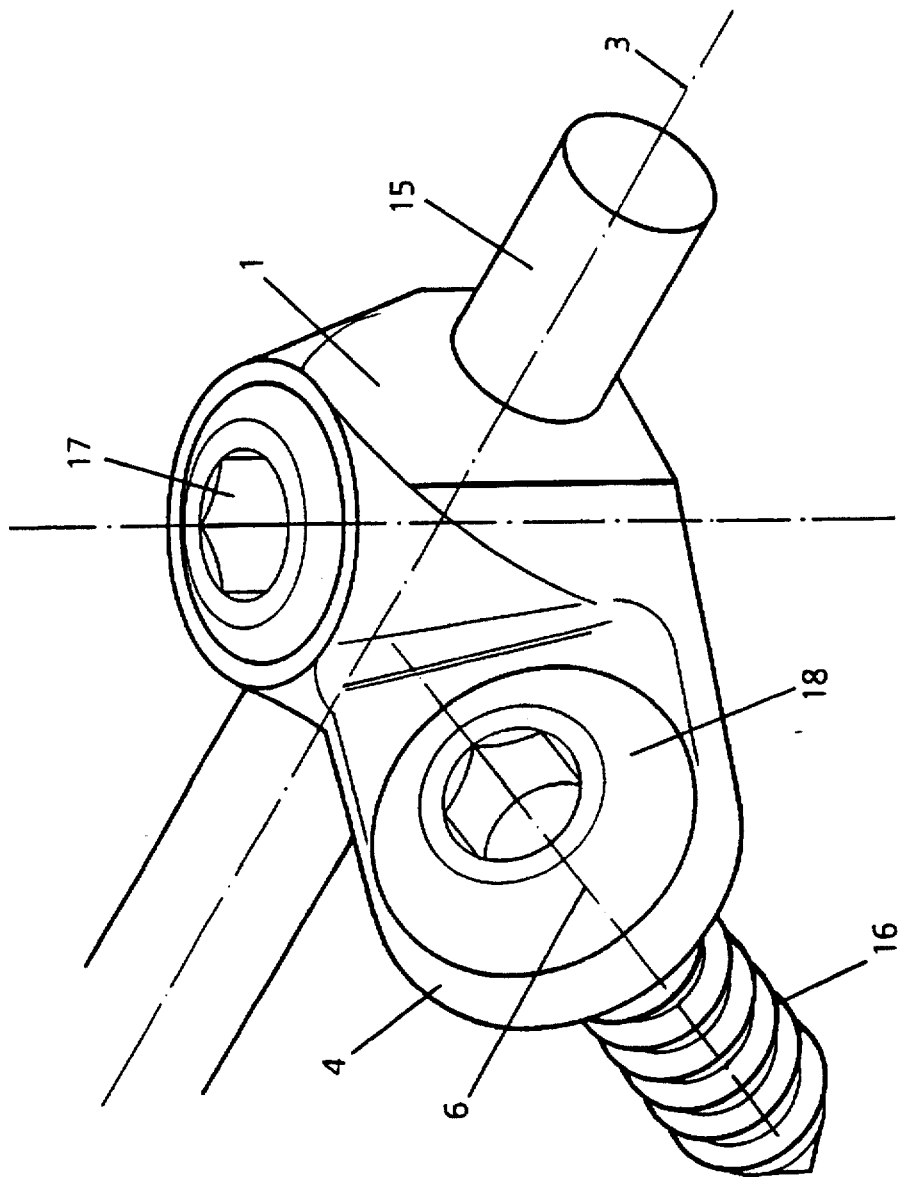
FIG. 4 is a perspective of the clamp of the invention with inserted longitudinal support and bone screw.

The clamp for a spinal affixation device shown in FIG. 1 essentially comprises a base body 1 crossed by a duct 2 of longitudinal axis 3 receiving a longitudinal support 15 (FIG. 4), further a substantially planar extension 4 continuing the base body 1 and crossed by a screw hole 5 of center axis 6 to receive a bone screw 16 (FIG. 4). Aside the components 15, 16 to be inserted, the clamp is therefore integral.

Figure 2:
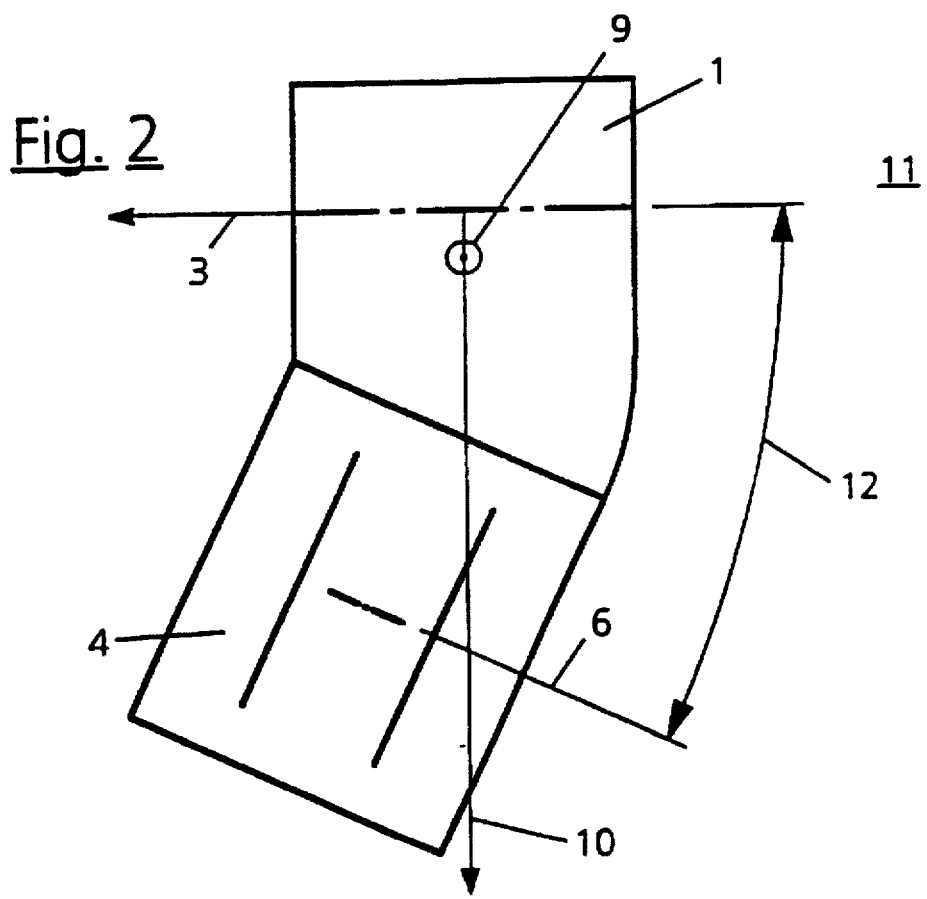
FIG. 2 is a projection on the horizontal plane of the clamp of FIG. 1.
Figure 3:
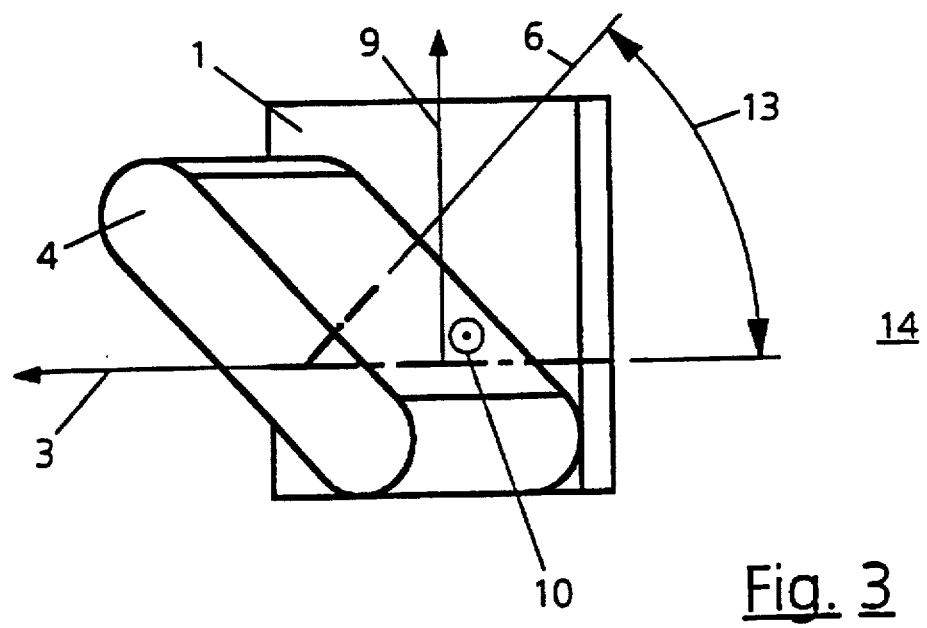
FIG. 3 is a sideways projection of the clamp of FIG. 1.

To elucidate the projections of the clamp shown in FIGS. 2 and 3, line 10 orthogonal to each of the longitudinal axes 3 and 9 and corresponding anatomically to the medio-lateral direction is represented.

FIG. 2 is a projection of the clamp on the plane 11 formed by the longitudinal axis 3 and the orthogonal line 10.

Accordingly the longitudinal axis 9 is perpendicular to the plane 11 corresponding to the plane of the drawing of FIG. 2. Anatomically the plane 11 corresponds to the median plane.

The duct 2 comprises means for rotationally and longitudinally locking a longitudinal support 15 inserted into said duct. Preferably these means are composed of a threaded borehole 8 in the base body 1 and evincing a longitudinal axis 9 orthogonal to the plane 11, an adjusting screw 17 (FIG. 4) being insertable into said borehole 8. Anatomically the longitudinal axis 9 corresponds to the dorsal direction.

The longitudinal axis 3—which anatomically corresponds to the cranial direction—and the center axis 6 constitute skewed straight lines of which the separation 7 is constant and in the range of 4 to 10 mm. Preferably the separation 7 is between 5 and 8 mm and typically between 5.8 and 6.7 mm.

The length of the duct 2 measured in the axial direction is 5 to 7 mm, preferably 5.7 to 6.4 mm. Said duct's diameter is 3.0 to 4.5 mm, preferably 3.2 to 3.8 (for instance 3.5 mm). In the embodiment shown in the drawing, the duct 2 is closed; however it may also comprise a side aperture (at the side of the base body 1 which is opposite the extension 4) to allow inserting a longitudinal support 15 also sideways through this aperture of the duct 2. This embodiment of the duct 2 further makes possible to intra-surgically modify the spinal affixation means without the need to completely disassemble said clamp, for instance without being required to entirely axially pull the longitudinal support 15 out of the duct 2.

The screw hole 5 is concave, preferably spherical, in the head seating zone for a bone screw to be inserted in order to allow some angulation of the bone screw 16 (FIG. 4) fitted with a spherical head 18.

The azimuth angle 12, between the longitudinal axis 6 and the longitudinal axis 3 and projected on this plane 11, is in the range of 20° to 30° for clamps used for the vertebra C3–C7. In the example shown, the azimuth angle is exactly 25°.

In other applications, for instance for the vertebra C2 as well as for the vertebra T1–T2, the azimuth angle 12 preferably is in the range of −5° to +5°.

FIG. 3 is a projection of the clamp onto the plane 14 passing through the longitudinal axis 3 and perpendicular to the orthogonal line 10. Plane 14 corresponds to the plane of the drawing of FIG. 3. Anatomically the plane 14 corresponds to the sagittal plane.

The cranial angle 13 between the longitudinal axis 6 and the longitudinal axis 3 projected on this plane preferably is in the range of 42.5° to 50.0° for clamps serving the vertebra C3–C7 as well as C2. In the example shown, the cranial angle 13 is exactly 47°49'.

The cranial angle 13 preferably is 80° to 100° for clamps serving the vertebra T1–T2.

The clamp shown in FIGS. 1–3 relates to a left-handed design. The corresponding right-hand design is implemented by mirroring the clamp at the plane 14 (sagittal plane), all geometric elations (spacings and angles) remain the same.

FIG. 4 shows the clamp together with the longitudinal support 15 locked in place by the adjusting screw 17 and moreover with a bone screw 16 having a spherical head 18 inserted through the extension 4.

Figure 5:
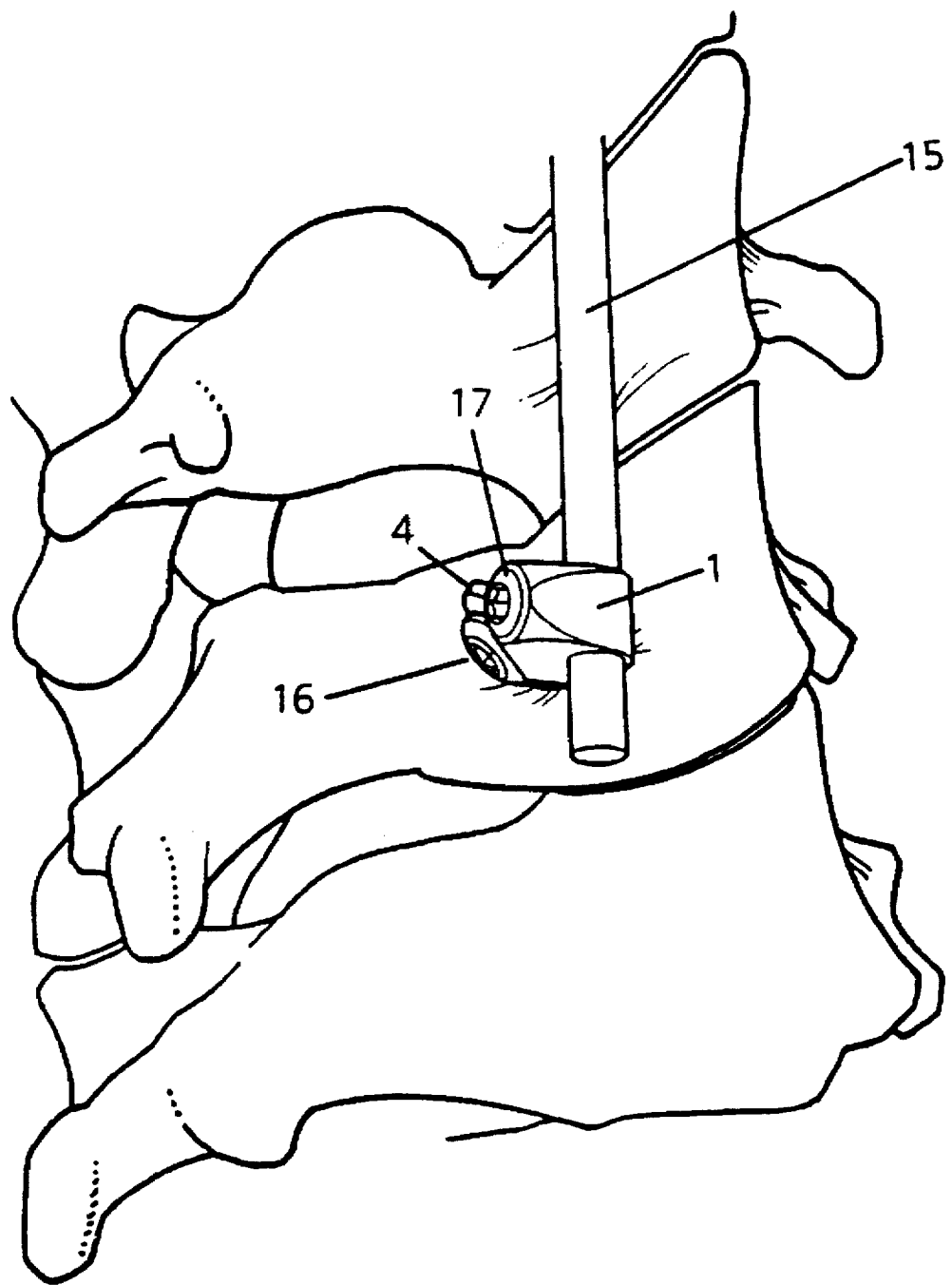
FIG. 5 is a perspective of the clamp of FIG. 4 with the bone screw anchored in a vertebra bone.

FIG. 5 shows the same clamp as FIG. 4 but now anchored by the bone screw inserted through the extension 4 into the vertebra 19. Connection with one or more clamps may be implemented using the longitudinal support 15 locked in place by the adjusting screw 17, said clamps being anchored by further bone screws into other vertebras.

In the clamp embodiment mode shown in FIGS. 1–5, the extension 4 is substantially planar and its plane runs at about 45° to the projection plane 11. However the extension 4 also may be in the form of a wedge, where preferably one wedge surface is parallel to the projection plane 11 and the other wedge surface is at an angle of about 45° to said projection plane 11. This latter embodiment offers the advantage that the clamp is able to rest against the vertebra by means of its wedge surface parallel to the projection plane 11.

EXAMPLES

Three specific illustrative designs of the clamps of the invention that offered especially good results are listed below.

Example 1

Length of duct 2: 6 mm
Cranial angle 13: 47.5°
Azimuth angle 12: 25°
Separation 7: 6.30 mm Example 2

Length of duct 2: 6 mm
Cranial angle 13: 45.0°
Azimuth angle 12: 0°
Separation 7: 6.15 mm Example 3

Length of duct 2: 6 mm
Cranial angle 13: 90.0°
Azimuth angle 12: 0°
Separation 7: 6.15 mm The clamp of the invention allows setting bone screws at a precisely defined angle relative to the anatomy in the region of the spine (cranial and azimuth angles) and thereby achieving reliable and stable anchoring in the bone. Illustratively the angles proposed by MAGERL may be used while being free of cumbersome positioning procedures.

The selected dimensions of the clamp of the invention allow sound complexing of bone chip and as a result good fusion is achieved. Corrections such as compression and traction also are feasible.

What is claimed is:

1. A clamp for a spinal affixation device comprising:

a base body crossed by a duct for receiving a longitudinal support, the duct having a duct longitudinal axis, and locking means to rotationally and longitudinally lock the longitudinal support to the body, the locking means having a locking means longitudinal axis; and a substantially tabular extension adjacent the base body and crossed by a screw hole for receiving a bone screw, the screw hole having a center axis, the tabular extension having upper and lower surfaces which are substantially parallel to each other;

wherein the duct longitudinal axis and the screw hole center axis are skewed straight lines that do not intersect, the extension is mounted at an angle of between 0° to 45° with respect to a plane of projection formed by the duct longitudinal axis and an orthogonal line perpendicular to both the duct longitudinal axis and the locking means longitudinal axis, and the duct longitudinal axis and the center axis are spaced by a distance of 4–10 mm.

2. The clamp of claim 1, wherein the duct longitudinal axis and the center axis are spaced by a constant distance of 5–8 mm.

3. The clamp of claim 1, wherein the length of the duct along the duct longitudinal axis is 5–7 mm.

4. The clamp of claim 1, wherein the duct has a diameter of 3–4.5 mm.

5. The clamp of claim 1, wherein the locking means includes a threaded borehole located within the base body and having a threaded borehole longitudinal axis coinciding with the locking means longitudinal axis and orthogonal to the plane of projection, and an adjusting screw received within the borehole.

6. The clamp of claim 1, wherein the screw hole is concave in a seating zone for a head of the bone screw that is inserted therein.

7. The clamp of claim 1, formed from a single piece of material.

8. The clamp of claim 1, wherein an azimuth angle subtended by the screw hole center axis and the duct longitudinal axis in the plane of projection formed by the duct longitudinal axis and the orthogonal line is within the range of +20° to +30.

9. The clamp of claim 1, wherein the azimuth angle subtended by the screw hole center axis and the duct longitudinal axis in the plane of projection formed by the duct longitudinal axis and the orthogonal line is within the range of −5° to +5°.

10. The clamp of claim 1, wherein a cranial angle subtended by the screw hole center axis and the duct longitudinal axis in the plane of projection formed by the duct longitudinal axis and the locking means longitudinal axis is within the range of 42.5° to 50°.

11. The clamp of claim 1, wherein a cranial angle subtended by the screw hole center axis and the duct longitudinal axis in the plane of projection formed by the duct longitudinal axis and the locking means longitudinal axis is within the range of 80° to 100°.

12. The clamp of claim 1, wherein the duct includes an aperture on the base body opposite the extension for receiving the longitudinal support.

\* \* \* \* \*